(12) United States Patent
Cronenberg (10) Patent No.: US 10,549,047 B2
(45) Date of Patent: *Feb. 4, 2020

(54) MEDICAL INJECTOR WITH RATCHETING PLUNGER

(71) Applicant: Becton, Dickinson and Company, Franklin Lakes, NJ (US)

(72) Inventor: Richard A. Cronenberg, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 137 days.

This patent is subject to a terminal disclaimer.

(21) Appl. No.: 15/494,752

(22) Filed: Apr. 24, 2017

(65) Prior Publication Data

US 2017/0224923 A1 Aug. 10, 2017

Related U.S. Application Data

(60) Continuation of application No. 14/580,159, filed on Dec. 22, 2014, now Pat. No. 9,707,353, which is a
(Continued)

(51) Int. Cl.
*A61M 5/31* (2006.01)
*A61M 5/315* (2006.01)

(52) U.S. Cl.
CPC ...... *A61M 5/31576* (2013.01); *A61M 5/3158* (2013.01); *A61M 5/31541* (2013.01);
(Continued)

(58) Field of Classification Search
CPC .. A61M 5/24; A61M 5/3158; A61M 5/31593; A61M 5/31555; A61M 5/31581;
(Continued)

(56) References Cited

U.S. PATENT DOCUMENTS 4,323,176 A * 4/1982 Sartain ............... B65D 83/0022
222/326
4,364,388 A 12/1982 Cech
(Continued)

FOREIGN PATENT DOCUMENTS

EP 0272035 A2 6/1988
EP 1923083 A1 5/2008
(Continued)

*Primary Examiner* — William R Carpenter
(74) *Attorney, Agent, or Firm* — Dickinson Wright PLLC (57) ABSTRACT

A medical injector, including a body with a displaceable plunger, which has at least one set of ratchet teeth, each set having a plurality of spaced-apart ratchet teeth disposed along the length thereof. At least one indexer is formed to engage the plunger. The indexer is configured to allow the plunger to displace distally toward the distal end of the body but not proximally toward the proximal end of the body. An actuator has a rocker pivotally connected thereto, the rocker being of single-piece construction and having an engagement portion formed to engage the ratchet teeth. The indexer and the rocker engage the same set of ratchet teeth. The rocker is pivotally connected at a first portion thereof to the body to rotate about an axis disposed on the body and pivotally connected at a second portion thereof to a link to rotate about an axis disposed on the link.

6 Claims, 9 Drawing Sheets

Related U.S. Application Data division of application No. 13/063,814, filed as application No. PCT/US2009/057429 on Sep. 18, 2009, now Pat. No. 8,936,578.

(60) Provisional application No. 61/192,468, filed on Sep. 18, 2008.

(52) U.S. Cl.
CPC .... *A61M 5/31555* (2013.01); *A61M 5/31581* (2013.01); *A61M 5/31595* (2013.01); *A61M 2005/3125* (2013.01); *A61M 2005/3126* (2013.01); *A61M 2205/583* (2013.01); *A61M 2205/584* (2013.01)

(58) Field of Classification Search
CPC .......... A61M 5/31585; A61M 5/31551; A61M 5/31578; A61M 2005/31508; A61M 5/3155

See application file for complete search history.

(56) References Cited

U.S. PATENT DOCUMENTS

| | | |
|---|---|---|
| 4,425,121 A | 1/1984 | Young et al. |
| 4,452,285 A * | 6/1984 | Leibhard .......... B05C 17/00516 |
| | | 141/392 |
| 4,820,287 A | 4/1989 | Leonard |
| 4,865,591 A | 9/1989 | Sams |
| 4,973,318 A | 11/1990 | Holm et al. |
| 5,224,936 A | 6/1993 | Gallagher |
| 5,433,352 A | 7/1995 | Ronvig |
| 5,496,293 A | 3/1996 | Huggenberger |
| 5,611,783 A | 3/1997 | Mikkelsen |
| 5,643,214 A | 7/1997 | Marshall et al. |
| 5,755,362 A | 5/1998 | Rodriguez et al. |
| 5,807,346 A | 9/1998 | Frezza |
| 5,891,106 A * | 4/1999 | Butuzov ................. A61M 5/24 |
| | | 604/209 |
| 6,004,297 A | 12/1999 | Steenfeldt-Jensen et al. |
| 6,439,439 B1 | 8/2002 | Rickard et al. |
| 6,613,023 B2 | 9/2003 | Kirchhofer et al. |
| 6,672,489 B1 | 1/2004 | Huang |
| 6,689,101 B2 | 2/2004 | Hjertman et al. |
| 6,699,224 B2 | 3/2004 | Kirchhofer et al. |
| 3,517,668 A1 | 7/2004 | Brickson |
| 6,793,646 B1 | 9/2004 | Giambattista et al. |
| 7,025,757 B2 | 4/2006 | Reilly et al. |
| 7,297,136 B2 | 11/2007 | Wyrick |
| 7,390,319 B2 | 6/2008 | Friedman |
| 7,678,084 B2 | 3/2010 | Judson et al. |
| 7,749,200 B2 | 7/2010 | Graf et al. |
| 7,771,399 B2 | 8/2010 | Burren et al. |
| 7,854,726 B2 | 12/2010 | Fago et al. |
| 7,867,197 B2 | 1/2011 | Sims et al. |
| 7,867,202 B2 | 1/2011 | Moser et al. |
| 7,993,301 B2 | 8/2011 | Boyd et al. |
| 8,038,655 B2 | 10/2011 | Burren et al. |
| 8,070,713 B2 | 12/2011 | Matusch |
| 8,167,849 B2 | 5/2012 | Boyd et al. |
| 8,267,900 B2 | 9/2012 | Harms et al. |
| 8,540,683 B2 | 9/2013 | Williams et al. |
| 8,672,899 B2 | 3/2014 | Atterbury et al. |
| 9,707,353 B2 * | 7/2017 | Cronenberg ...... A61M 5/31555 |
| 2001/0051792 A1 | 12/2001 | Kirchhofer et al. |
| 2002/0007142 A1 | 1/2002 | Hjertman et al. |
| 2002/0016571 A1 | 2/2002 | Kirchhofer et al. |
| 2002/0165500 A1 | 11/2002 | Bechtold et al. |
| 2005/0154351 A1 | 7/2005 | Graf et al. |
| 2005/0177115 A1 * | 8/2005 | Broennimann ... A61M 5/31525 |
| | | 604/208 |
| 2007/0043319 A1 | 2/2007 | Kimmel et al. |
| 2007/0232998 A1 | 10/2007 | Yang et al. |
| 2007/0233004 A1 | 10/2007 | Sims et al. |
| 2008/0071227 A1 | 3/2008 | Moser et al. |
| 2008/0077094 A1 | 3/2008 | Burren et al. |
| 2010/0094206 A1 | 4/2010 | Boyd et al. |
| 2010/0105003 A1 | 4/2010 | Weil et al. |
| 2011/0034870 A1 | 2/2011 | Glejboel et al. |

FOREIGN PATENT DOCUMENTS

| | | | |
|---|---|---|---|
| FR | 2913341 A1 | 9/2008 | |
| JP | U-S61-008055 | 1/1986 | |
| JP | U-H05-062255 | 8/1993 | |
| JP | H09-503150 A | 3/1997 | |
| JP | 2006204918 A | 8/2006 | |
| JP | 2007534345 A | 11/2007 | |
| JP | 2008119075 A | 5/2008 | |
| JP | 2010509958 A | 4/2010 | |
| WO | WO-9406494 A1 | 3/1994 | |
| WO | WO-9413339 A1 | 6/1994 | |
| WO | WO-9607443 A1 | 3/1996 | |
| WO | WO-02070049 A1 | 9/2002 | |
| WO | WO-03020347 A2 | 3/2003 | |
| WO | WO-2006079900 A2 | 8/2006 | |
| WO | WO-2008058668 A1 | 5/2008 | |
| WO | WO-2009121194 A1 * | 10/2009 | ........ A61M 5/31555 |
| WO | WO-2010033770 A2 | 3/2010 | |
| WO | WO-2011039215 A1 | 4/2011 | |

\* cited by examiner

MEDICAL INJECTOR WITH RATCHETING PLUNGER

RELATED APPLICATIONS

This application is a continuation of currently pending U.S. patent application Ser. No. 14/580,159, filed on Dec. 22, 2014, which is a division of U.S. patent application Ser. No. 13/063,814, filed on Apr. 27, 2011 and issued on Jan. 20, 2015 as U.S. Pat. No. 8,936,578, which is the U.S. national stage of international patent application number PCT/US2009/057429, filed on Sep. 18, 2009, which claims the benefit of U.S. provisional patent application Ser. No. 61/192,468, filed on Sep. 18, 2008. Each of the disclosures of these applications is hereby incorporated herein by reference in its entirety.

FIELD OF THE INVENTION

This invention relates to displaceable medical injector plungers and, more particularly, to ratcheting medical injector plungers.

BACKGROUND OF THE INVENTION

Medical injectors are well known in the art including syringes and pen injectors. Medical injectors typically include a plunger for advancing one or more stoppers in delivering a medicament during an injection. Although it is known in the prior art to provide syringe plungers with teeth or other features to prevent retraction and re-use after an initial injection, syringe plungers are typically actuated through direct application of linear force. Dose size is a direct function of plunger displacement. It may be difficult to control linear displacement of the plunger, thus, resulting in difficulty over control of dose size.

As for pen injectors, a lead screw or other rotating plunger is provided which is mechanically coupled to a dose-setting knob or other actuator through a series of mechanical connections. The typical pen injector mechanism is fairly complex and consists of multiple cooperating parts. For costs reasons and simplicity of use, a minimum number of working parts is desired.

SUMMARY OF THE INVENTION

A medical injector is provided herein having a body with a displaceable plunger. The plunger includes a plurality of spaced-apart ratchet teeth disposed along the length thereof. At least one indexer is provided formed to engage the plunger, wherein the indexer is configured to allow the plunger to displace distally toward a distal end of the body but not proximally toward a proximal end of the body. The medical injector also includes an actuator having an engagement portion formed to engage one or more of the ratchet teeth. The actuator is displaceable to a ready state, the engagement portion being displaced proximally relative to the plunger with the actuator being displaced to the ready state. The indexer prevents proximal movement of the plunger thereby allowing the engagement portion to by-pass one or more of the ratchet teeth with the actuator being displaced to the ready state. In addition, the actuator is displaceable from the ready state to cause actuation of the medical injector. The displacement from the ready state causes distal displacement of the engagement portion with the engagement portion engaging one or more of the ratchet teeth and causing distal displacement of the plunger with the engagement portion. Advantageously, the subject invention provides a plunger for a medical injector which may be controllably advanced with a minimum number of cooperating parts.

These and other features of the invention will be better understood through a study of the following detailed description and accompanying drawings.

DETAILED DESCRIPTION OF EMBODIMENTS OF THE INVENTION

With reference to the figures, a medical injector 10 is shown having a ratchetable plunger 12 provided therewith. As will be appreciated by those skilled in the art, the medical injector 10 may be of various forms, including being a syringe or pen injector. In accordance with the subject invention, the medical injector 10 is particularly well-suited for administering at least one fixed dose, even better suited for administering a series of fixed doses. The medical injector 10 may be configured in any way known to be compatible with the plunger 12 as described herein. The medical injector 10 may include a reservoir 14 for accommodating an injectable medicament, which may be a drug cartridge or formed directly in the medical injector 10. The reservoir 14 may have one or more stoppers 16 associated therewith as known in the art. The medical injector 10 may be also provided with a needle 18 for injection which may be removably attached or affixed to the medical injector 10 such as in a "staked" arrangement.

Figure 2:
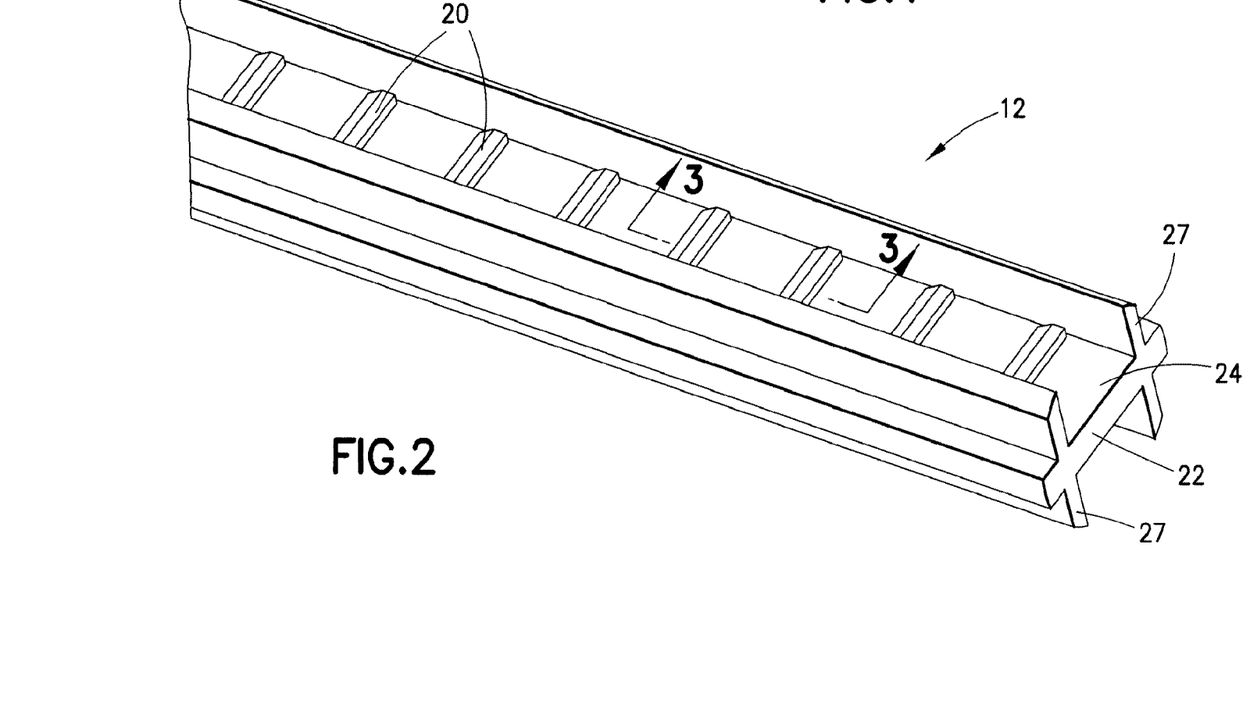
FIG. 2 is a plunger useable with the subject invention.

The plunger 12 is elongated and generally flat. A plurality of spaced-apart ratchet teeth 20 are disposed along the length of the plunger 12. In a preferred arrangement, the plunger 12 includes a plate-shaped body 22 having opposing first and second faces 24, 26. The ratchet teeth 20 are disposed on the first face 24 and, in a further preferred arrangement, also on the second face 26. Preferably, the ratchet teeth 20 on the first and second faces 24, 26 are axially aligned along the length of the plunger 12.

Figures 3, 4:
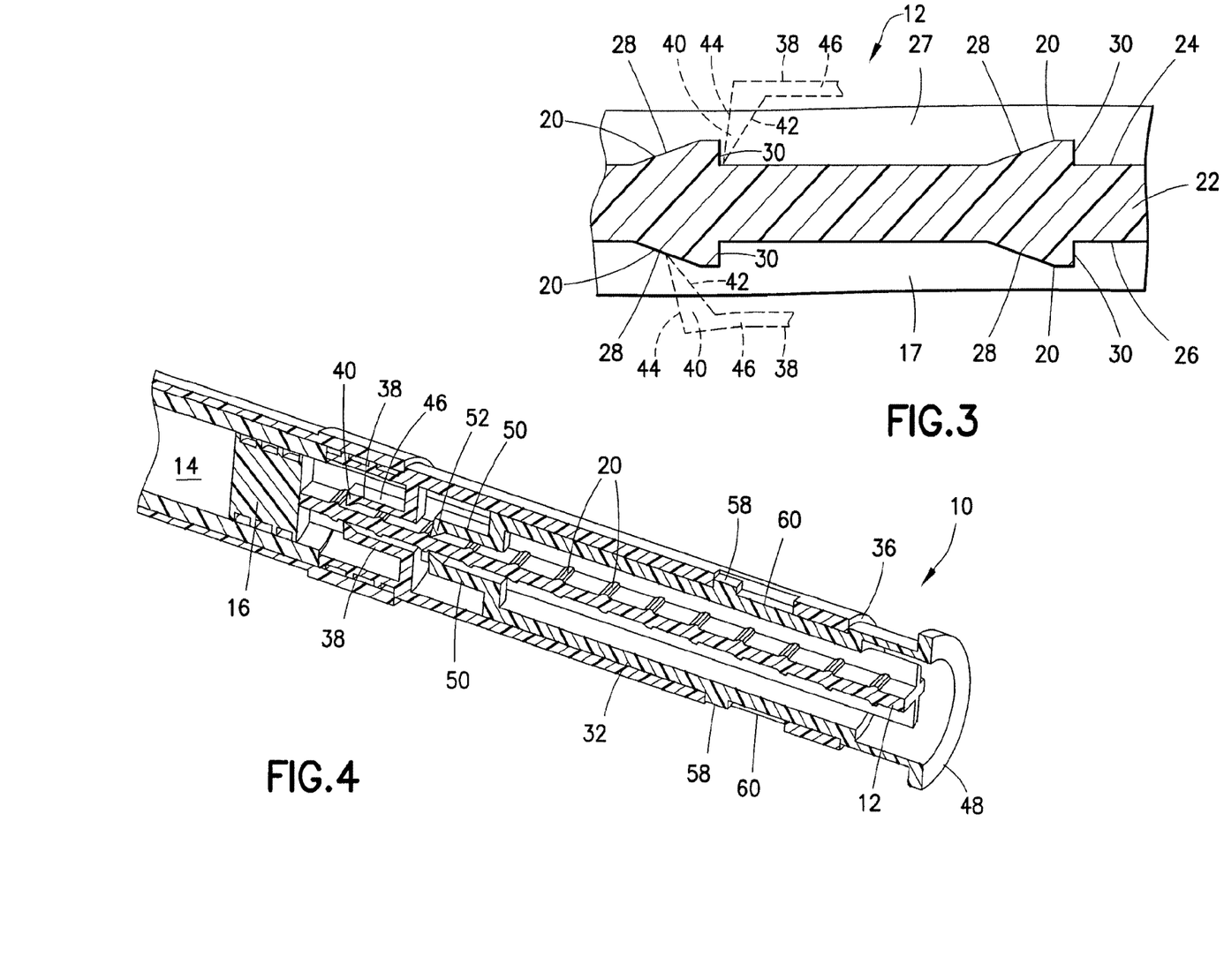
FIG. 3 is a cross-sectional view taken along line 3-3 of FIG. 2.
FIGS. 4-6 show operation of a medical injector formed in accordance with the subject invention.

The ratchet teeth 20 are configured to permit unidirectional movement of the plunger 12. Particularly, with reference to FIG. 3, the ratchet teeth 20 are preferably saw-tooth shaped having a ramped surface 28 and a shoulder stop 30. As shown in FIG. 3, the ramped surfaces 28 of the ratchet teeth 20 on both the first and second surfaces 24, 26 are oriented to face in the same general direction. The shoulder stops 30 extend transversely from the first and second faces 24, 26, preferably at a substantially perpendicular orientation.

The plunger 12 may also have one or more rails 27 extending from the first face 24 and/or the second face 26. The rails 27 may be formed to slide through one or more corresponding shape-mating slots formed in the medical injector 10. The rails 27 may provide stability during use, particularly during translation of the plunger 12.

Figure 1:
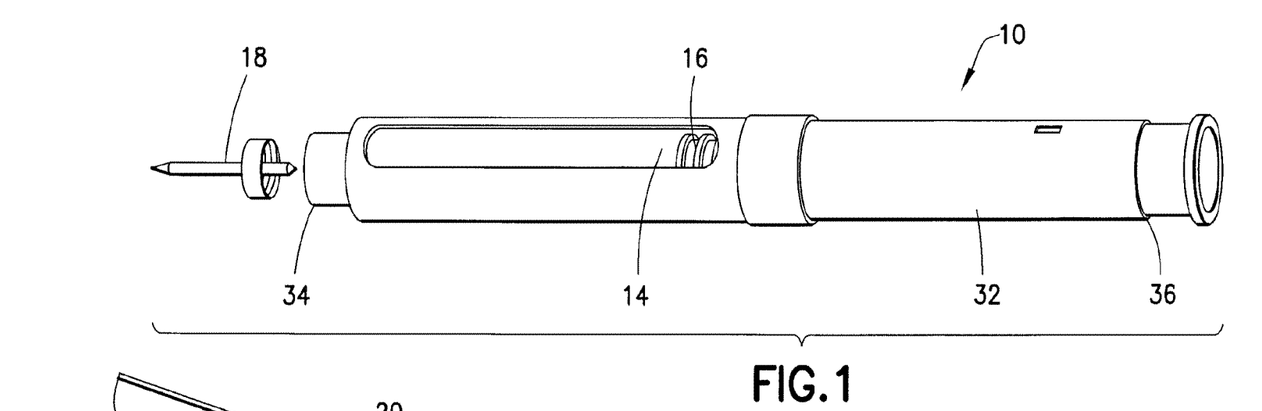
FIG. 1 is a perspective view of a medical injector formed in accordance with the subject invention.
Figures 5, 6:
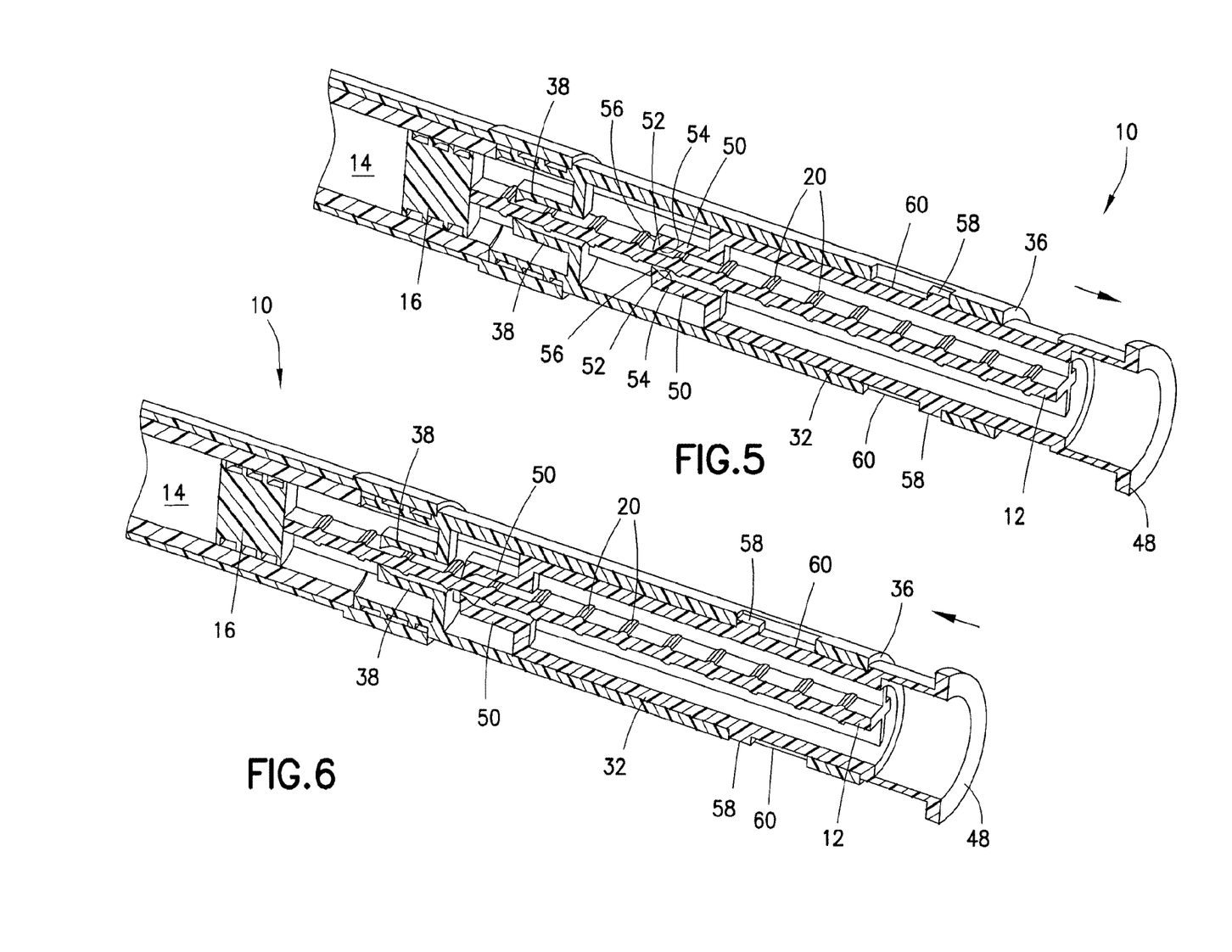

With reference to FIGS. 4-6, the plunger 12 is disposed in a body 32 of the medical injector 10. The body 32 includes a distal end 34, located to be directed toward a patient during an injection, and a proximal end 36, located to be away from a patient during an injection (FIG. 1). During use, the medical injector 10 is configured to permit the plunger 12 to move unidirectionally therein in a distal direction toward the distal end 34, but not in a proximal direction toward the proximal end 36. To facilitate such unidirectional movement, at least one indexer 38 is provided formed to engage the plunger 12. The indexer 38 is configured to allow the plunger 12 to displace distally toward the distal end 34 of the body 32 but not proximally toward the proximal end 36 of the body 32.

The indexer 38 includes a deflectable pawl 40 which, as shown schematically in FIG. 3, includes a ramped engagement surface 42 and an outward facing stop surface 44. The indexer 38 is outwardly deflectable to permit the engagement surface 42 to ascend the ramped surface 28 of an individual of the ratchet teeth 20 with the plunger 12 moving distally relative thereto. With sufficient distal movement, the indexer 38 by-passes the ratchet teeth 12, and under inherent resilience of the indexer 38, snaps inwardly such that the stop surface 44 is aligned with the shoulder stop 30. Preferably, the stop surface 44 is formed to be generally parallel to the shoulder stop 30. With rearward (proximal) movement of the plunger 12, the shoulder stop 30 and the stop surface 44 interferingly engage thus preventing proximal movement of the plunger 12. In a preferred embodiment, a pair of the indexers 38 are provided so as to act against the ratchet teeth 20 located on both the first and second faces 24, 26, as shown in FIGS. 4-6. It is further preferred that a pair of the indexers 38 be provided which are axially aligned thus providing a pinching effect to the plunger 12. This pinching effect may provide a stable holding force for the plunger 12.

The indexer 38 may be formed to be deflectable through inherent resilience, such as through material selection (e.g., being formed of a thermoplastic). In addition, or alternatively, the indexer 38 may include a cantilevered arm 46 which permits deflection of the associated pawl 40. The indexer 38 is formed to have a natural, unbiased state as shown in FIGS. 4-6, where the indexer 38 is positioned to act against the shoulder stop 30 of the ratchet teeth 20. The cantilevered arm 46 is formed with sufficient internal memory to provide the unbiased state for the indexer 38.

The medical injector 10 also includes an actuator 48 having an engagement portion 50 formed to engage one or more of the ratchet teeth 20. The engagement portion 50 preferably includes an engagement pawl 52 having a ramped engagement surface 54 and an outward facing stop surface 56 configured like the pawl 40 described above. Preferably, two of the engagement portions 50 are provided located to engage the ratchet teeth 20 located on the first and second faces 24, 26.

With reference to FIG. 4, the plunger 12 is positioned to engage one of the stoppers 16. To cause actuation of the medical injector 10, as shown in FIG. 5, the actuator 48 is moved to a ready state, with the engagement portion 50 moving proximally. The indexer 38 prevents proximal movement of the plunger 12, thus allowing the actuator 48 to move proximally relative to the plunger 12. With the plunger 12 being held stationary, and the engagement portion 50 moving proximally relative to the plunger 12, the engagement portion 50 by-passes one or more of the ratchet teeth 20. The actuator 48 is displaced sufficiently to achieve a ready state.

For actuation of the medical injector 10, the actuator 48 is displaced from the ready state with distal movement of the engagement portion 50. The engagement portion 50 engages one or more of the ratchet teeth 20, particularly with interfering engagement between the shoulder stop 30 and the stop surface 56. In particular, the engagement portion 50 engages the next distal ratchet tooth 20. Distal movement of the engagement portion 50 causes the plunger 12 to move distally therewith. Distal movement of the plunger 12, in turn, causes distal advancement of the stopper 16 in causing an injection to be administered. The ratchet teeth 20 are able to by-pass the indexer 38 in the distal direction.

The size of a dose to be administered by the medical injector 10 is a function of the spacing between the ratchet teeth 20 and/or the amount of proximal displacement of the engagement portion 50 relative to the ratchet teeth 20 with the actuator 48 moving to a ready state. To create a fixed dose, one or more keys 58 may be defined on the medical injector 10 and/or the actuator 48 which are formed to nest within and slide along corresponding channels 60 formed in the medical injector 10 and/or the actuator 48. As shown in FIGS. 4-6, it is preferred that the keys 58 be formed on the actuator 48 and the channels 60 be formed in the medical injector 10. With reference to FIG. 4, the keys 58 are at the distal end of the channel 60, prior to use. With proximal displacement of the actuator 48, the keys 58 are proximally advanced in the channels 60 to a proximalmost position corresponding to the ready state of the actuator 48. The length of the travel of the keys 58 in the channels 60 restricts the range of movement of the actuator 48 in defining the size of the dose administrable by the medical injector 10. As shown in FIGS. 5 and 6, the keys 58 are advanced distally with the actuator 48 during use to a distalmost position.

Figure 7:
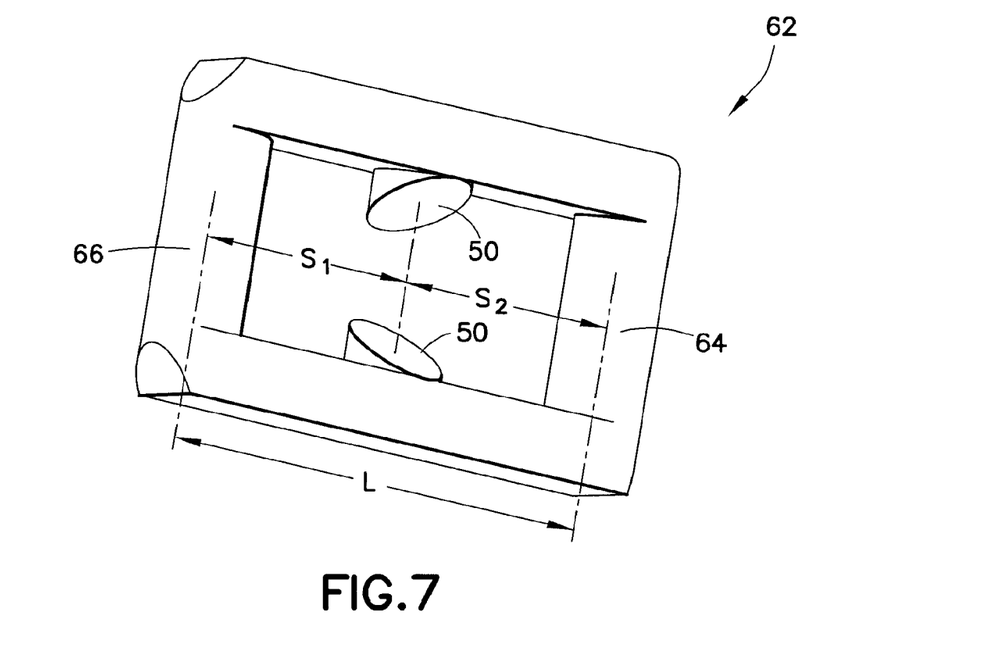
FIGS. 7-8 show two different rockers useable with the subject invention.
Figure 8:
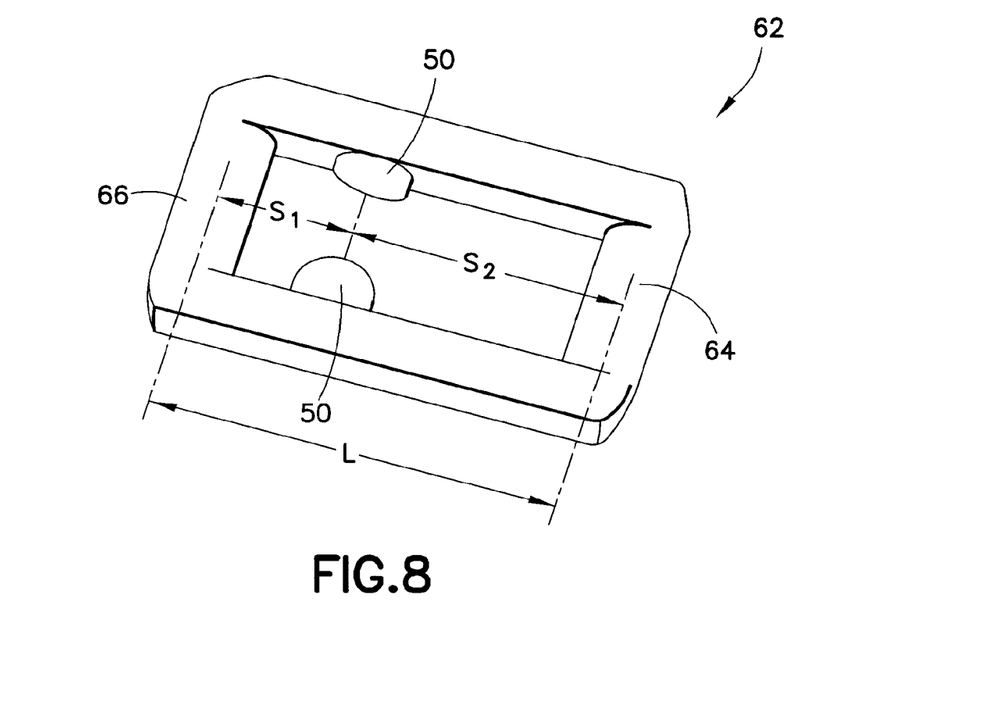

The actuator 48 shown in FIGS. 4-6 is a linear slide actuator which applies force directly to the plunger 12. As will be appreciated by those skilled in the art, the actuator 48 may be of various configurations. With reference to FIGS. 7-8, the actuator 48 may include a rocker 62 pivotally mounted thereto. The rocker 62 is frame-shaped having a first end 64 for pivotal mounting to the actuator 48 and a second opposing end 66 for pivotally mounting to the medical injector 10. The engagement portion 50 is located between the first and second ends 64, 66. As shown in FIGS. 7-8 two of the engagement portions 50 may be provided to coact with the ratchet teeth 20 being located on the first and second faces 24, 26.

It is noted that the spacing between the first and second ends 64, 66 affects force transmission from the actuator 48 to the plunger 12 particularly in the generation of torque. The spacing L between the first and second ends 64, 66, as well as the spacing S1, S2 of the engagement portion 50 from the first and second ends 64, 66, affects how torque is generated and transmitted to the plunger 12.

Figure 9:
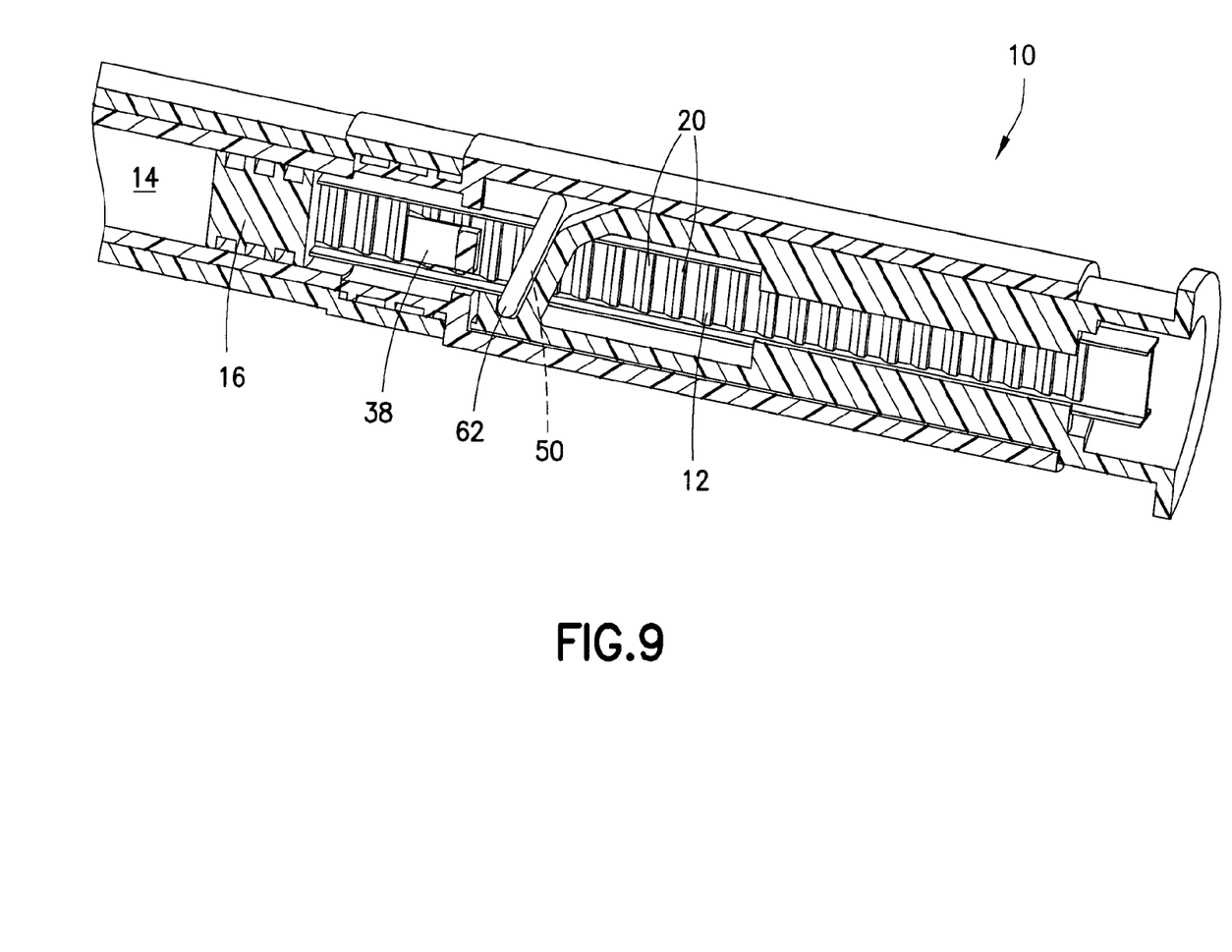
FIGS. 9-11 show operation of a medical injector formed in accordance with the subject invention using a rocker.
Figure 10:
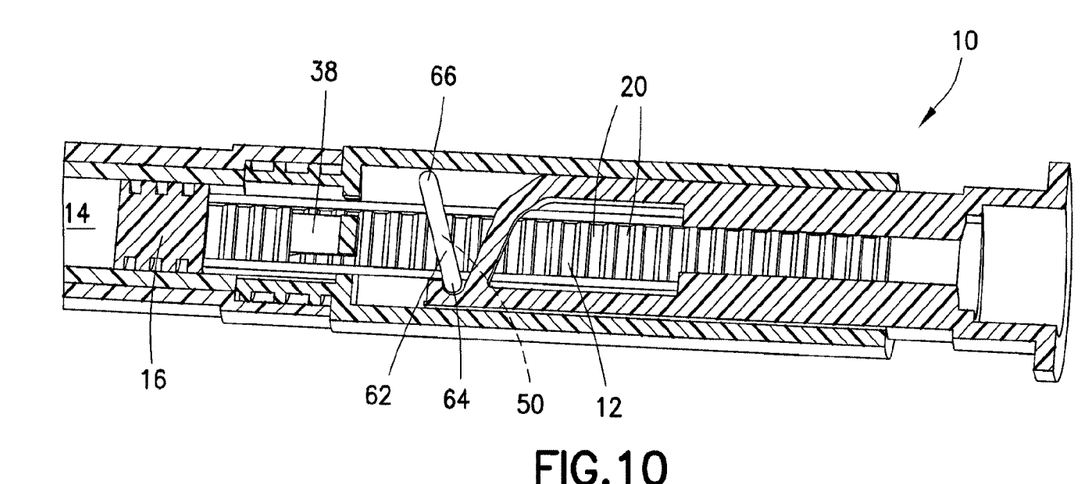
Figure 11:
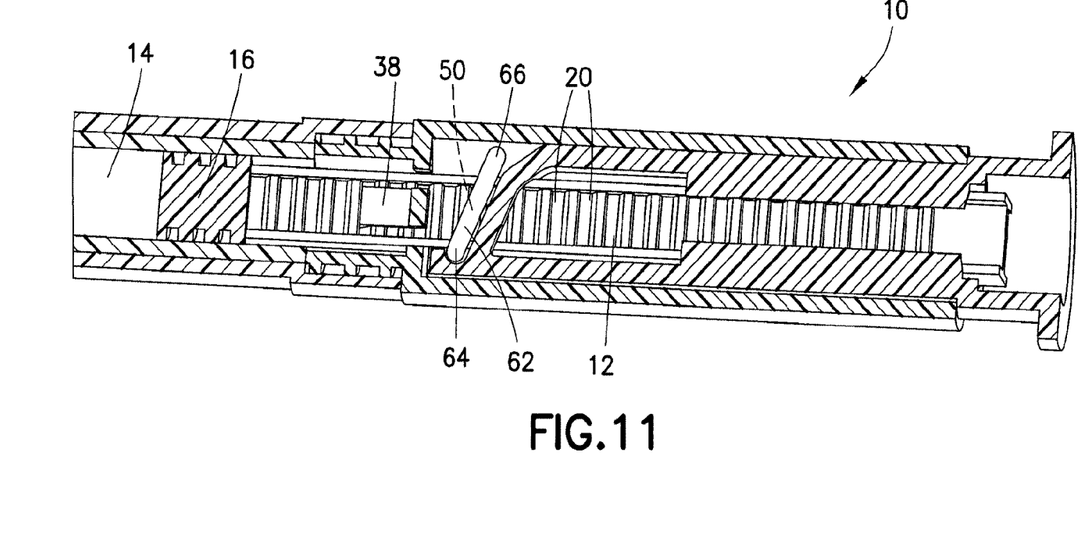

With reference to FIG. 9, the actuator 48 is shown in an initial pre-use state with the rocker 62 being inclined distally. With reference to FIG. 10, the actuator 48 has been advanced to the ready state with the rocker 62 having been drawn proximally with rotation about the second end 66 so as to be inclined in a proximal direction. During this movement, the engagement portion 50 by-passes one or more of the ratchet teeth 20 in the same manner as described above. As shown in FIG. 11, the actuator 48 is displaced from the ready state to cause actuation of the medical injector 10. With displacement of the actuator 48 from the ready state, the rocker 62 is caused to advance distally about the second end 66 with the engagement portion 50 causing the plunger 12 to also advance distally. Dose size may be restricted both by the key 58/channel 60 arrangement described above and/or by the range of motion of the rocker 62.

Figure 12:
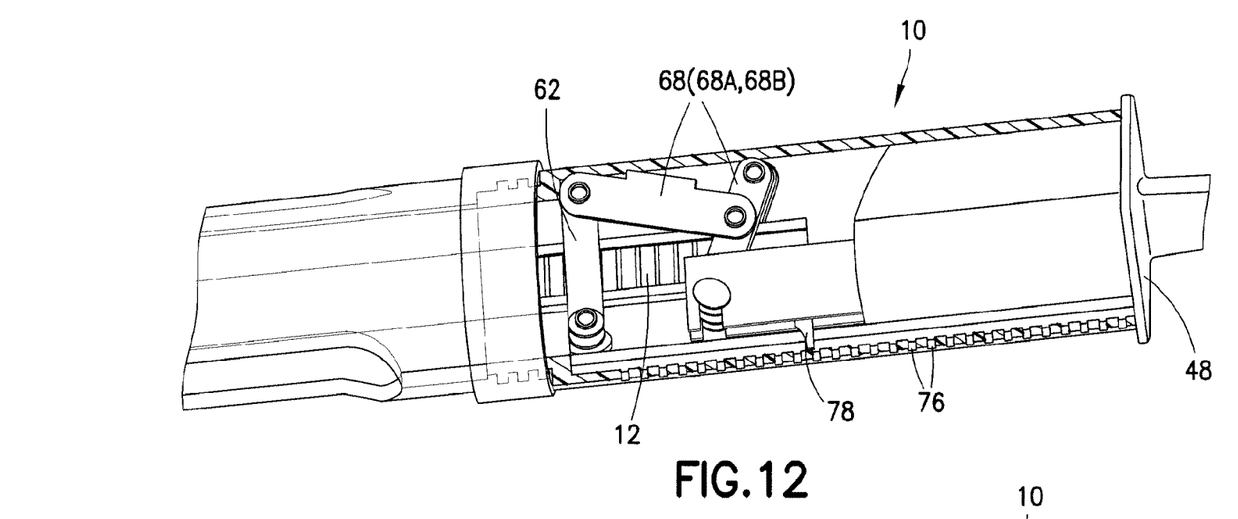
FIGS. 12-13 show the use of a multi-link rocker in accordance with the subject invention.
Figure 13:
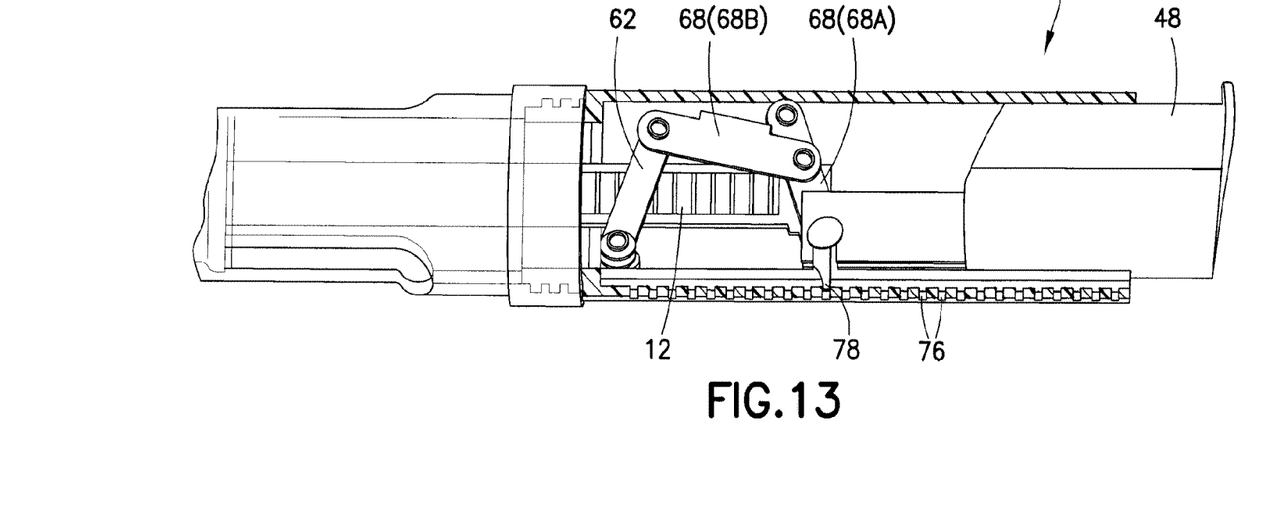

As will be appreciated by those skilled in the art, the rocker 62 may be directly coupled to the actuator 48, as shown in FIGS. 9-11. As will be appreciated by those skilled in the art, a multi-link arrangement may be used to couple the rocker 62 to the actuator 48. With reference to FIGS. 12-13, one or more links 68 may be connected between the rocker 62 and the actuator 48 to provide force for displacement thereof. Any arrangement of the links 68 may be utilized which transmits force from the actuator 48 to the rocker 62. As shown in FIGS. 12-13, two of the links 68 (68A, 68B) are utilized with the link 68A being pivotally connected to the actuator 48 and pivotally connected to the link 68B, and with the link 68B being pivotally connected to the link 68A and pivotally connected to the rocker 62. The links 68A, 68B collectively transmit force to the rocker 62.

Figure 15:
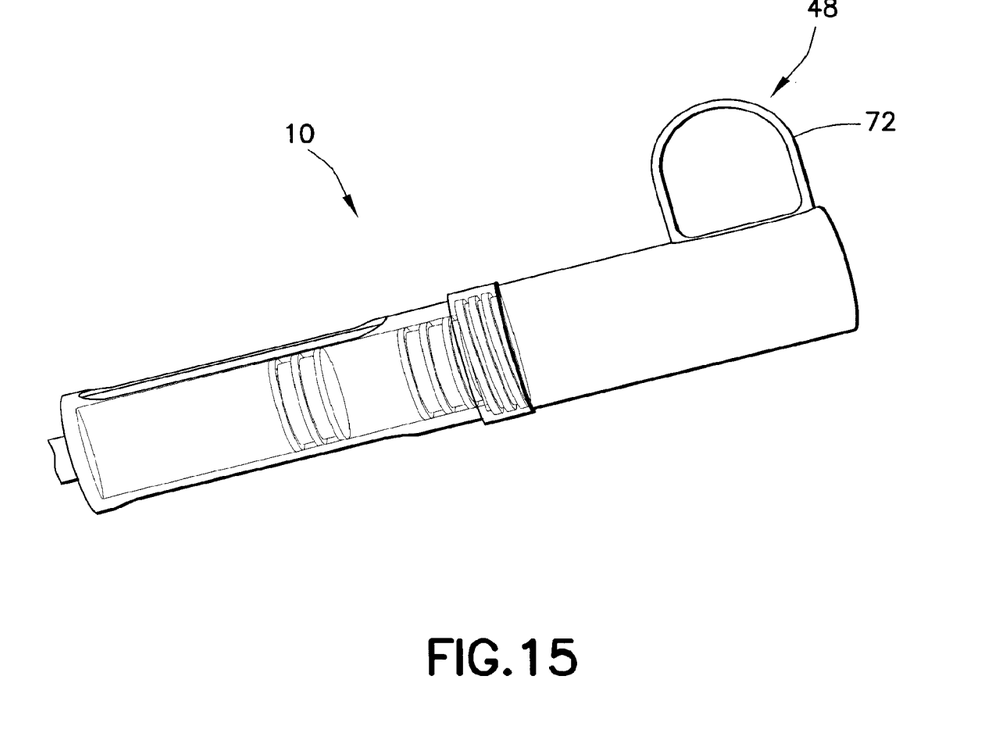
FIGS. 15-17 show the use of a pivotable actuator useable with the subjection invention.
Figure 16:
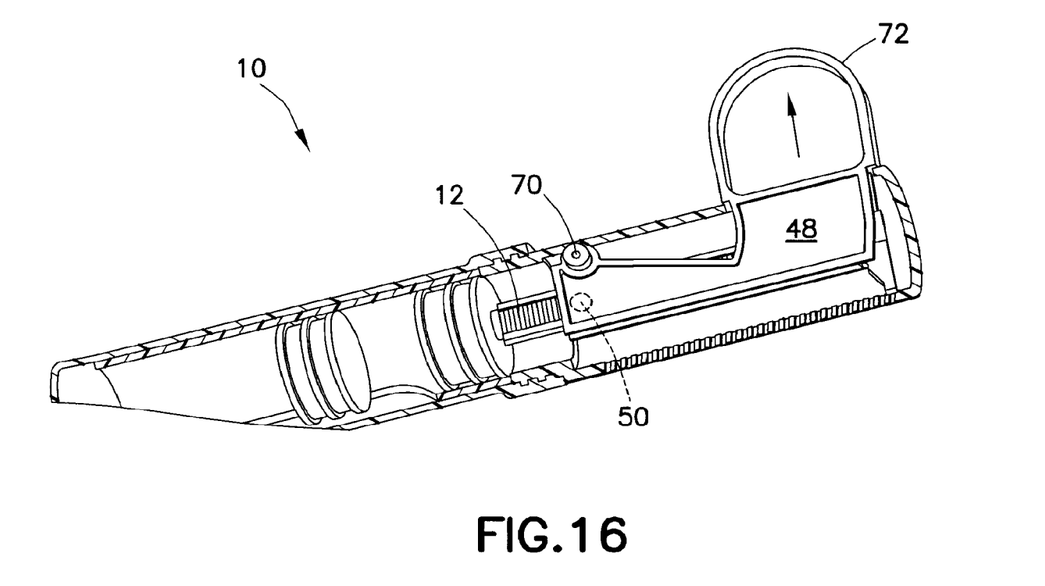
Figure 17:
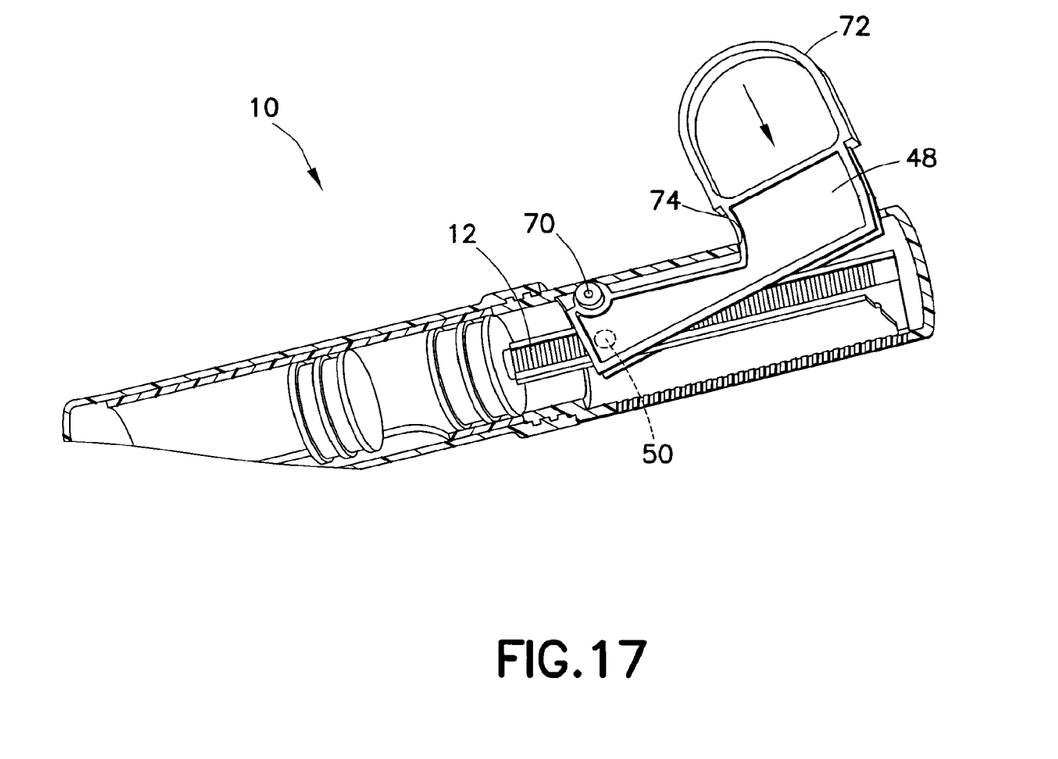

With reference to FIGS. 15-17, the actuator 48 may be arranged to be non-linearly displaced. As shown in FIGS. 15-17, the actuator 48 may be formed to pivot about a fulcrum 70. With the actuator 48 pivoting outwardly from the medical injector 10 about the fulcrum 70, the engagement portion 50 is caused to be displaced proximally. Conversely, inward pivoting of the actuator 48 about the fulcrum 70 causes distal displacement of the engagement portion 50. The engagement portion 50 coacts with the plunger 12 in the same manner as described above.

With reference to FIGS. 15 and 16, the medical injector 10 is shown in a pre-use state. To facilitate handling of the actuator 48, a grip ring or pad 72 may be provided which extends radially outwardly from the medical injector 10 to facilitate displacement of the actuator 48. To prepare for use, as shown by the arrow in FIG. 16, the actuator 48 is pivoted to a ready state as shown in FIG. 17. To cause actuation of the medical injector 10, the actuator 48 is pivoted inwardly from the ready state, as shown by the arrow in FIG. 17. The size of the dose may be fixed with the actuator 48 being pivotable by limiting the range of rotation of the actuator 48. A portion 74 of the medical injector 10 may be configured to limit the range of rotation of the actuator 48, particularly outward rotation, such limited range corresponding to the ready state.

Figure 14:
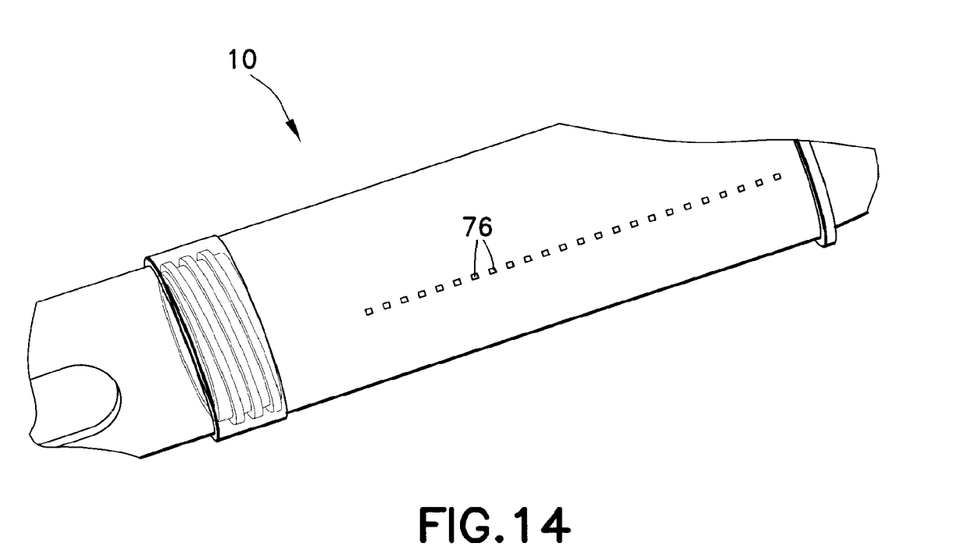
FIG. 14 shows a dose counter useable with the subject invention.

As will be appreciated by those skilled in the art, the medical injector 10 may be utilized with various features. With reference to FIGS. 12-14, a dose counter may be provided with the medical injector 10 which gives an indication of the number of available doses to be administered. For example, a series of dose indicating holes 76 may be formed in the medical injector 10, particularly to be visible from the outside thereof. A pointer 78 may be provided on the actuator 48 which is formed to be visible through a single of the dose indicating holes 76 at a given instance. During use, with the plunger 12 being distally advanced dose by dose, the pointer 78 is likewise advanced along the series of the dose indicating holes 76. The number of the dose indicating holes 76 located distally of the pointer 78 provides as an indication of the remaining number of doses. With the pointer 78 appearing in the distalmost of the dose indicating holes 76, indication is provided of no remaining available doses for administration.

It is preferred that the pointer 78 be formed of a contrasting color relative to the portion of the medical injector 10 located about the dose indicating holes 76 such that the pointer 78 is readily visible through the dose indicating holes 76.

What is claimed is:

1. A medical injector comprising:
a body having a distal end and a proximal end;
a displaceable plunger disposed in the body, the plunger having at least one set of ratchet teeth, each set having a plurality of spaced-apart ratchet teeth disposed along the length thereof;
at least one indexer formed to engage the plunger, wherein the indexer is configured to allow the plunger to displace distally toward the distal end of the body but not proximally toward the proximal end of the body; and
a linearly displaceable actuator having a rocker pivotally connected thereto, the rocker being of single-piece construction and having an engagement portion formed to engage one or more of the ratchet teeth; wherein
the actuator is proximally displaceable to a ready state, the engagement portion being displaced proximally relative to the plunger with the actuator being proximally displaced to the ready state, the indexer preventing proximal movement of the plunger thereby allowing the engagement portion to by-pass one or more of the ratchet teeth with the actuator being displaced to the ready state;
the actuator is displaceable from the ready state to cause actuation of the medical injector, the displacement from the ready state causing distal displacement of the engagement portion with the engagement portion engaging one or more of the ratchet teeth and causing distal displacement of the plunger with the engagement portion;
the indexer and the rocker engage the same set of ratchet teeth; and
the rocker is pivotally connected at a first portion thereof to the body to rotate about an axis disposed on the body and pivotally connected at a second portion thereof to a link to rotate about an axis disposed on the link.

2. A medical injector as in claim 1, wherein the link is pivotally connected directly to the actuator.

3. A medical injector as in claim 1, wherein the actuator is slidably displaceable relative to the body.

4. A medical injector as in claim 3, wherein at least one key is formed to extend from the actuator or the body and a channel is formed in the other of the actuator and the body, the key being configured to be slidably received in the channel.

5. A medical injector as in claim 1, wherein the actuator is linearly displaceable relative to the body.

6. A medical injector comprising:
a body having a distal end and a proximal end;
a displaceable plunger disposed in the body, the plunger having at least one set of ratchet teeth, each set having a plurality of spaced-apart ratchet teeth disposed along the length thereof;
at least one indexer formed to engage the plunger, wherein the indexer is configured to allow the plunger to displace distally toward the distal end of the body but not proximally toward the proximal end of the body; and an actuator having a rocker pivotally connected thereto, the rocker being of single-piece construction and having an engagement portion formed to engage one or more of the ratchet teeth; wherein the actuator is displaceable to a ready state, the engagement portion being displaced proximally relative to the plunger with the actuator being displaced to the ready state, the indexer preventing proximal movement of the plunger thereby allowing the engagement portion to by-pass one or more of the ratchet teeth with the actuator being displaced to the ready state;

the actuator is displaceable from the ready state to cause actuation of the medical injector, the displacement from the ready state causing distal displacement of the engagement portion with the engagement portion engaging one or more of the ratchet teeth and causing distal displacement of the plunger with the engagement portion;

the indexer and the rocker engage the same set of ratchet teeth;

the rocker is pivotally connected at a first portion thereof to the body to rotate about an axis disposed on the body and pivotally connected at a second portion thereof to a link to rotate about an axis disposed on the link; and a plurality of dose indicating holes are formed in the body, and wherein a pointer extends from the actuator, the pointer being configured to be visible through a single one of the dose indicating holes at an instance, the pointer providing indication of the remaining number of doses in the medical injector.

* * * * *